(12) United States Patent
Guibert et al.

(10) Patent No.: US 6,730,114 B1
(45) Date of Patent: May 4, 2004

(54) LOW POWER PULSED FLASH HOT AIR TECHNIQUE

(75) Inventors: Raul Guibert, Falls Church, VA (US); Bettina Guibert, Falls Church, VA (US)

(73) Assignee: Vanny Corporation, Falls Church, VA (US)

(*) Notice: Subject to any disclaimer, the term of this patent is extended or adjusted under 35 U.S.C. 154(b) by 0 days.

(21) Appl. No.: 10/264,595

(22) Filed: Oct. 4, 2002

Related U.S. Application Data

(60) Provisional application No. 60/327,199, filed on Oct. 5, 2001.

(51) Int. Cl.[7] .................................................. A61F 7/00
(52) U.S. Cl. .............................. 607/96; 607/108; 607/98
(58) Field of Search ............................... 607/96, 98, 99, 607/108–112

(56) References Cited

U.S. PATENT DOCUMENTS 2,706,988 A * 4/1955 Weber ......................... 607/107
3,082,540 A * 3/1963 Hiltenbrand .................. 34/554
3,816,940 A * 6/1974 Cournoyer ..................... 34/101

* cited by examiner

*Primary Examiner*—Roy D. Gibson
(74) *Attorney, Agent, or Firm*—Birch, Stewart, Kolasch & Birch, LLP

(57) ABSTRACT

The Flash Technique is a new concept in thermodynamics. This technique of accumulating heat energy in a small air plenum being instantaneously flashed over the problem region of the body in a thermowave manner is capable of accomplishing with high efficiency and simultaneously Thermotherapy, Immunetherapy and Chemotherapy treatments in the patients' own home. The term "problem region" refers to tumors, a set of muscles, or any other site causing difficulty and which lends to the use of instantaneous high temperature air pulse flashes. The low power and the small size and weight of this home unit lend to the use of a flexible belt to support two applicators against different parts the body.

12 Claims, 6 Drawing Sheets

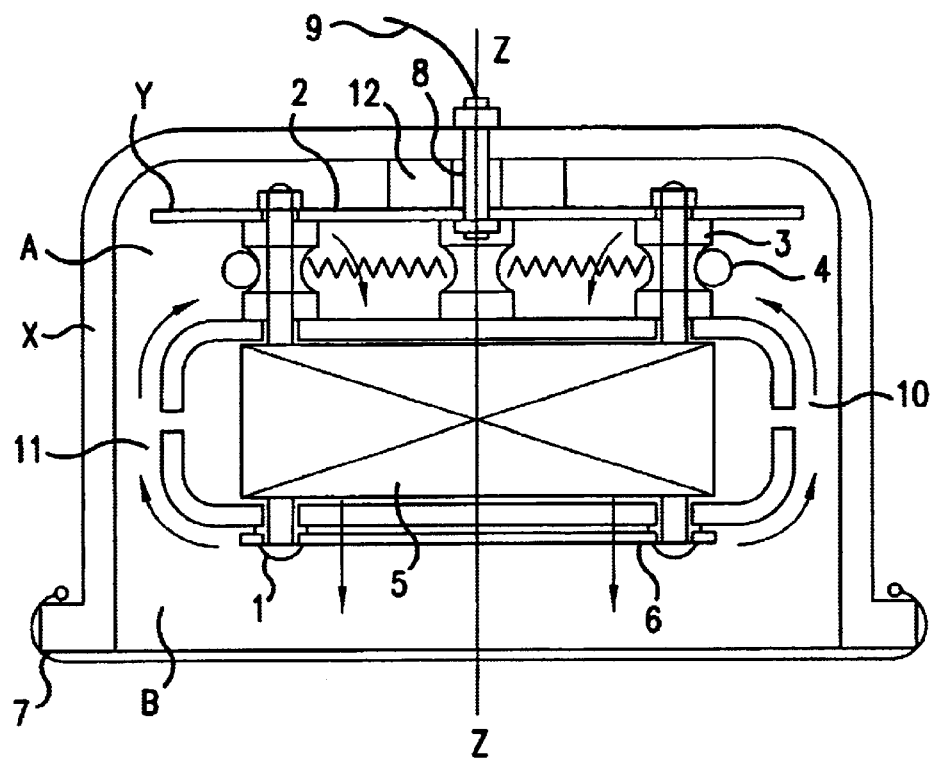
FIG.1A
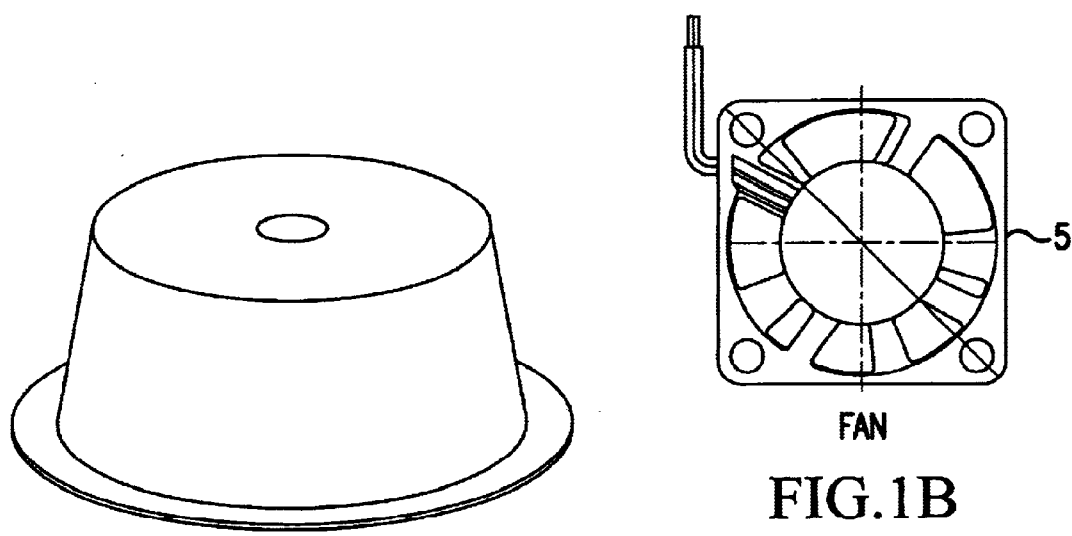
FIG.2
FIG.1B

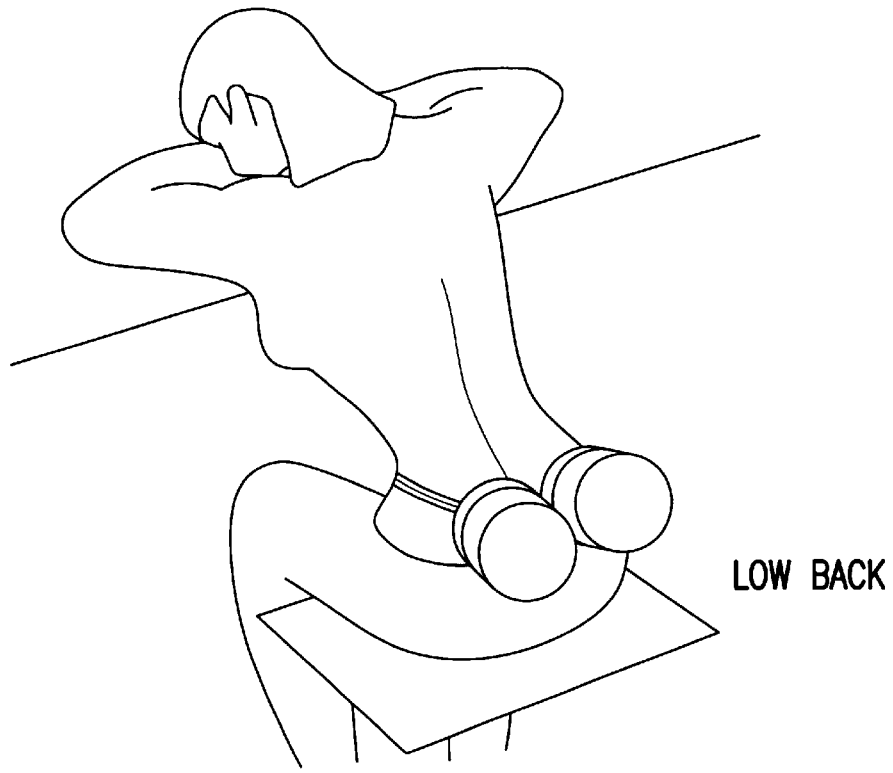
LOW BACK
FIG.7A
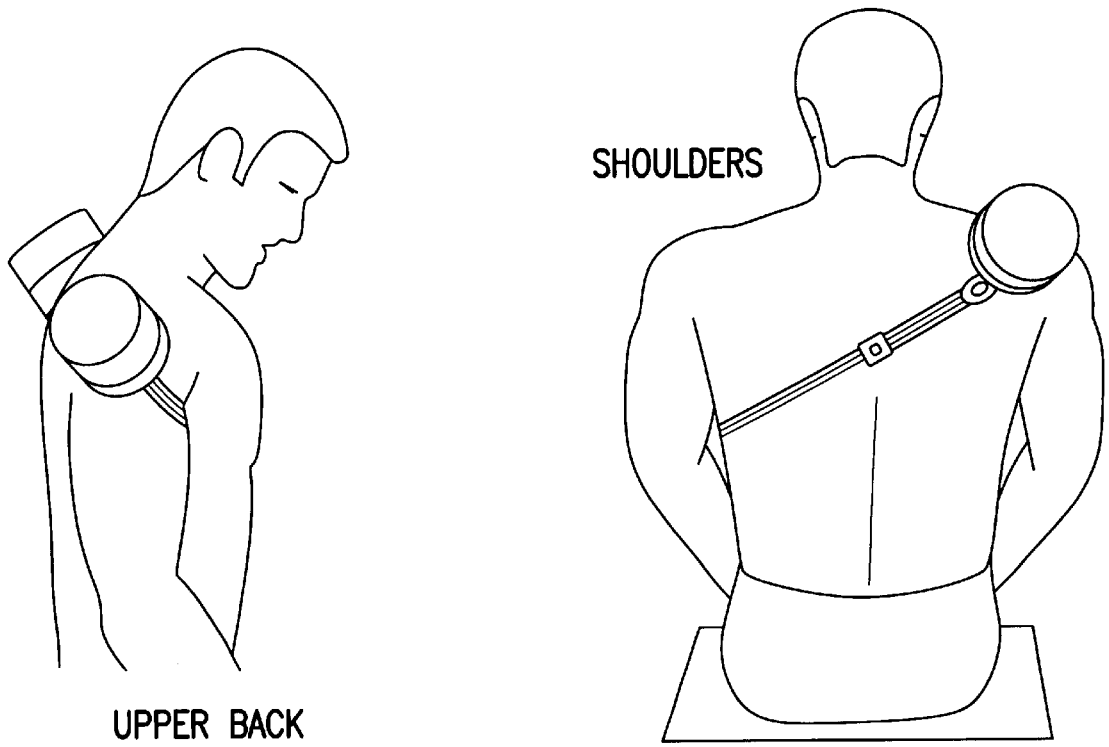
UPPER BACK
FIG.7B
SHOULDERS
FIG.7C

LOW POWER PULSED FLASH HOT AIR TECHNIQUE

The present invention claims priority under 35 USC 119 on provisional application U.S. Application No. 60/327,199 filed Oct. 5, 2001.

BACKGROUND OF INVENTION

1. Field of Invention

This invention relates to a technique to obtain the most efficient results when Thermotherapy, Immunotherapy, or Chemotherapy treatments are performed and the media is hot air. Hot air, in order to be highly efficient, requires a high peak of temperature of 130° F.±10%, and the air in contact with the skin must have a minimum air velocity of 600 feet per minute±10% for a fast convection. The Flash action in the thermowave has a duration of a fraction of a second. The relaxation cooling period between FLASH peaks is 22 seconds±10%, going gradually from the FLASH peak temperature of 130 F. to 120 F. by mixing with the air in plenum B.±10%.

2. Description of the Related Art

In each Flash pulse the heat is transferred to a layer under the skin and each fine layer acts as a source of heat to transfer to the next layer and that is why it is so important that the Flash peak temperature obtain the conduction from layer to layer for the best penetration to reach the skin sensors and lesion for the transdermal drug delivery of the Chemotherapy treatment, Guibert U.S. Pat. No. 5,443,487 "Combine Chemo-Thermo Therapy Technique" and U.S. Pat. No. 6,328,711 B1 "Chemo-Thermo Applicator for Cancer Treatment". Also of prior art interest are the Guibert U.S. Pat. Nos. 5,447,530 and 5,580,350 "Periodic pulsed heat technique for inducing analgesic effects".

SUMMARY OF INVENTION

The invention improves heat penetration into the tissues of the body without creating damage on the skin or discomfort to the patient when the applicator is applied directly on top of the skin and the media is hot air. For efficiency, high peaks and low power supply are the main objective of this invention by the creation of two well defined plenums on the applicator, according to the description and figures. The way it was solved is by using a DC axial tube fan sandwiched between two separator discs creating well defined positive and negative air plenums. The negative plenum encloses the air among the PCBA discs, the disc is attached to the negative pressure side of the fan and the dome wall. The positive plenum encloses the air among the disc attached to the positive pressure side of the fan, the body skin or plastic film and the dome wall. The negative plenum when the fan is OFF and the heater is ON is the one that accumulates the heat at the maximum allowed temperature, at this time activates the temperature sensor putting OFF the heater and ON the fan. When the fan starts the FLASH action drawing the hot air into the positive plenum almost immediately the peak temperature is transferred for an instant to the skin (one second or less) and the air drawn from the negative plenum circulates back through a narrow passage between the edges of the two discs and the wall allowing a certain time, 10 seconds±10% to equalize the temperatures of the two plenums.

The control box contains a 12 VDC 1.3 AH rechargeable battery with an AC/DC charger which is required together with an ON and OFF recycling relay delay timer and an ON/OFF delay timer for the 20/30 minute treatment. The battery could be replaced by an AC/DC power supply. The control box has an ON/OFF switch and light leds to show the unit functioning.

BRIEF DESCRIPTION OF THE DRAWINGS

For better understanding of the invention as well as other objects and further features thereof, reference is made to the following detailed description to be read in conjunction with the accompanying drawings, wherein:

FIG. 1A is a cross section of the applicator in the longitudinal line in accordance with the invention.

FIG. 1B is a cross section of the fan.

FIG. 2 is a perspective view of the applicator dome.

FIGS. 7A, 7B and 7C show treatment on different parts of the body.

DETAILED DESCRIPTION OF THE INVENTION

Figure 3:
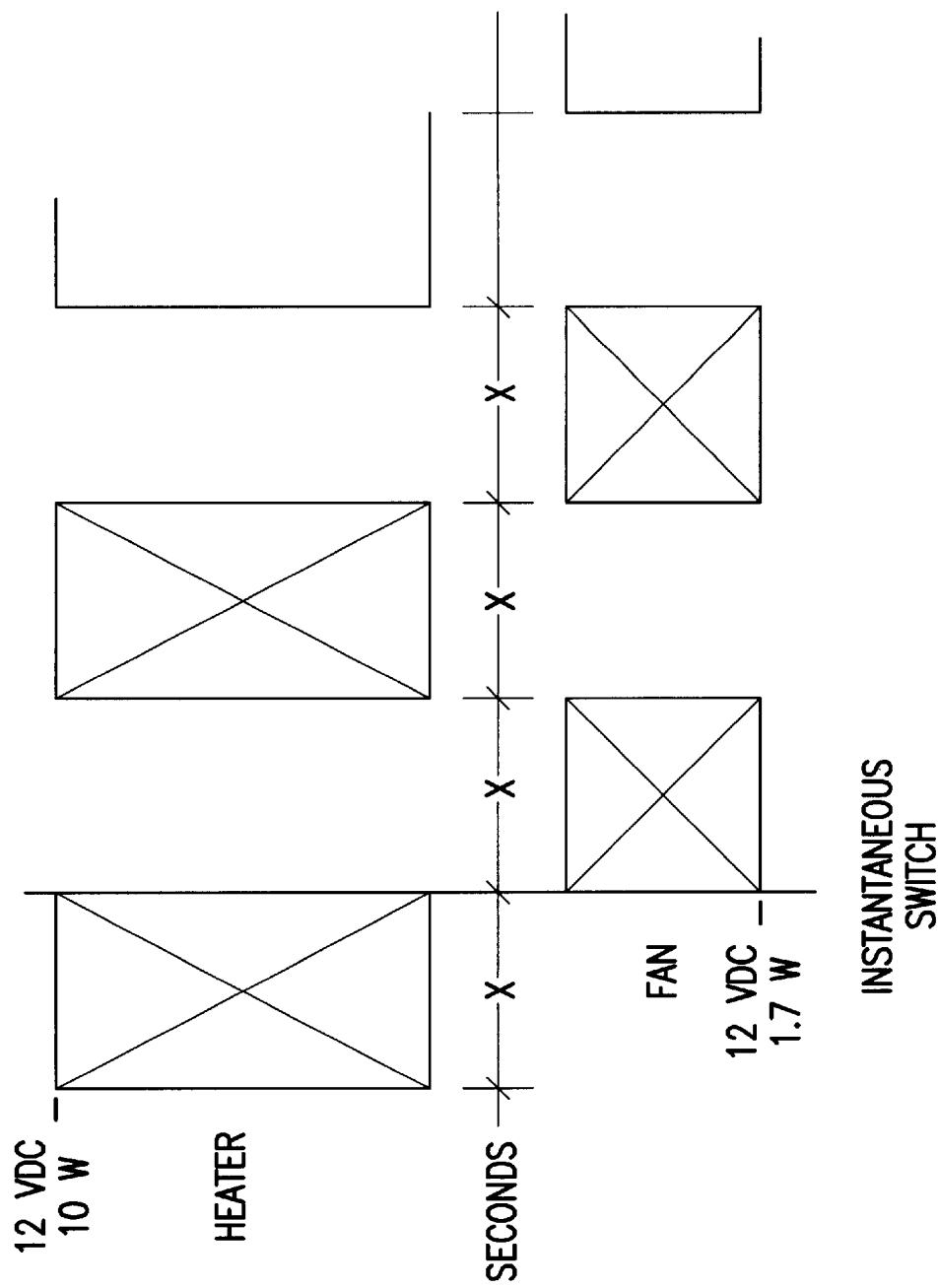
FIG. 3 is a block diagram of power and cycling times of fan and heater.

In reference to FIG. 1, which shows a cross section of the applicator with the two main components: a casing dome X, and an integrated module Y. The dome FIG. 2 is produced in one piece in polycarbonate, a similar type of plastic, or in aluminum. The approximate size of the dome in the case of a home unit could be in the range of 3.25" ID by 2" high. Owing to the need for a hermetic unit in contact with the skin, a nitril 7, or similar plastic film can be attached to the lower edges of the dome.

The integrated module Y is attached to the center-line of the roof of the dome by means of a Screw or rivet 8, applicator cross section FIG. 1. Module Y components from top to bottom are: four screws and nuts 1, holding all the parts in the central axis, a PCBA (printed circuit board assembly) 2, on a disc which OD (outside diameter) is ⅛", smaller of the dome ID (inside diameter), four ceramics 3, supporting the heater coil 4, the ceramics are in contact on one side with the PCBA disc, and on the other side with a separator disc, FIG. 2, and fan.

When the module Y is assembled to the roof of dome X, two well defined plenums, A and B are determined by the discs, and the walls of the dome X.

These two plenums intercommunicate through the space 10, defined by the two discs and the wall of the dome X.

Plenum A is in the negative side of the fan, plenum B in the positive side of the fan.

The plenum (A) is formed by the PCBA 2, the shape disc 11 on the suction side of the fan, the fan and the dome wall. The PCBA holds the sensor of the temperature control, the thereto-fuse and the electronic connections on the side of the PCBA facing the plenum, four ceramics 3, determine the height of plenum A and supports the heater coil 4. Plenum (B) is formed by the shape disc 11, the positive side of the fan, the dome wall and the skin or the nitril 7 or plastic film. The height must be equal to the height of plenum A, ½"±10%.

The plenums A and B are important elements to the FLASH Technique as a new concept in Thermodynamics.

Two instantaneous sequences are determined by a timing relay control that puts ON the heater and the fan OFF at the same time and for the predetermined time duration of 12 seconds±10%, followed by the heater ON and the fan OFF for the same time duration. This time relay action determines the air thermo-wave over the skin. The Block Diagram is shown in FIG. 3. When the heater is ON and the fan is OFF the heater will supply the amount of heat necessary to raise the temperature of Plenum A to 130° F.±10%.

A precise thermo-switch with ON and OFF contacts located in plenum A can replace the time relay, the thermo-switch will open and close when the air in plenum A reach the peak temperature at that instant will put OFF the heater and ON the fan to produce the Flash action. The complete module is the heart of the unit and will be attached to the top of the dome X by means of a screw or rivet integrating the complete unit ready to function. Owing to the need for a hermetic unit in contact with the skin a Nitril film was specially designed to have a flexible seal FIG. 1. Nitril is one of the different plastics or types of rubber that can be used.

The dome may be produced in one piece in polycarbonate or similar type of plastic or in aluminum due to the small size of the unit, in the case of a home unit 3¼ inches ID and 2 inches high. The control box is separated, connected to the module by a three fine wire cable.

Figure 4:
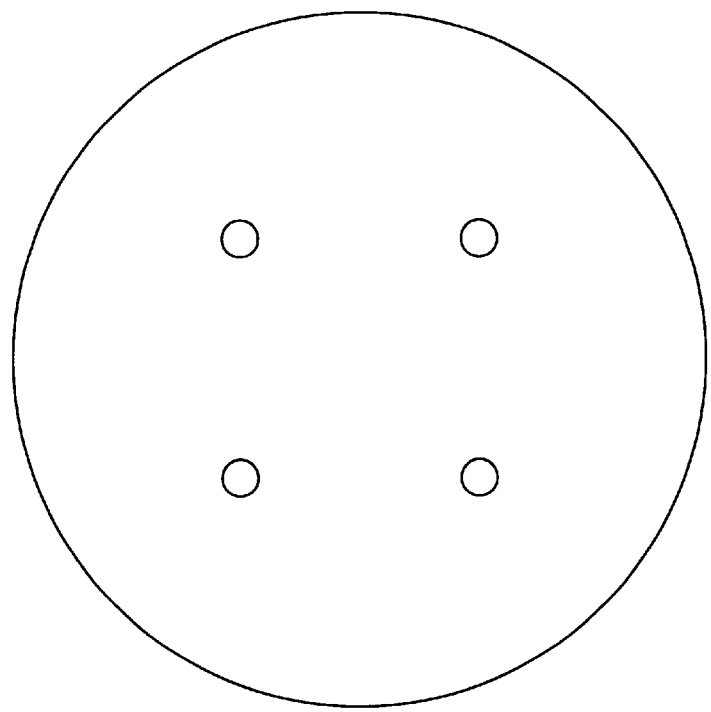
FIG. 4 is the PCBA disc made of fenolic or similar without showing the electric circuitry.
Figure 5:
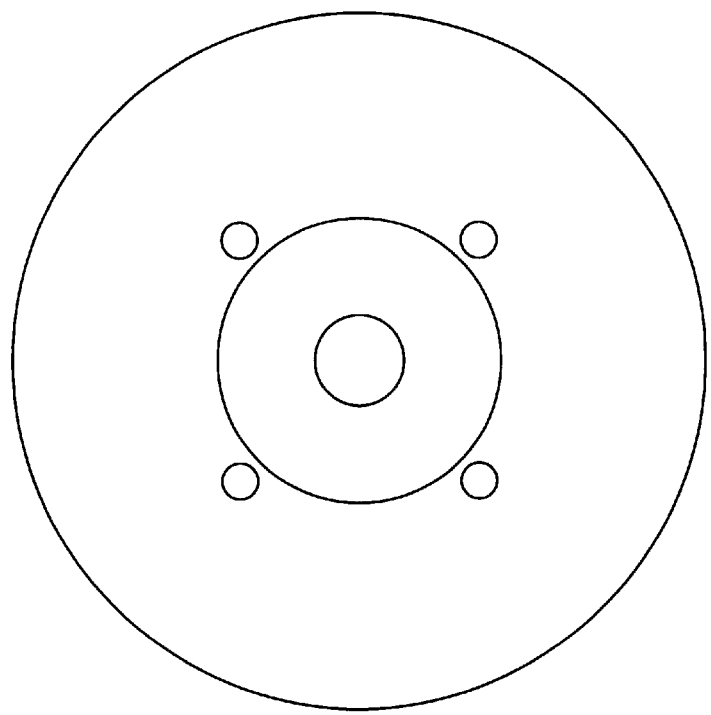
FIG. 5 the discs separators of plenum A and B, when sandwiching the fan.
Figure 6A:
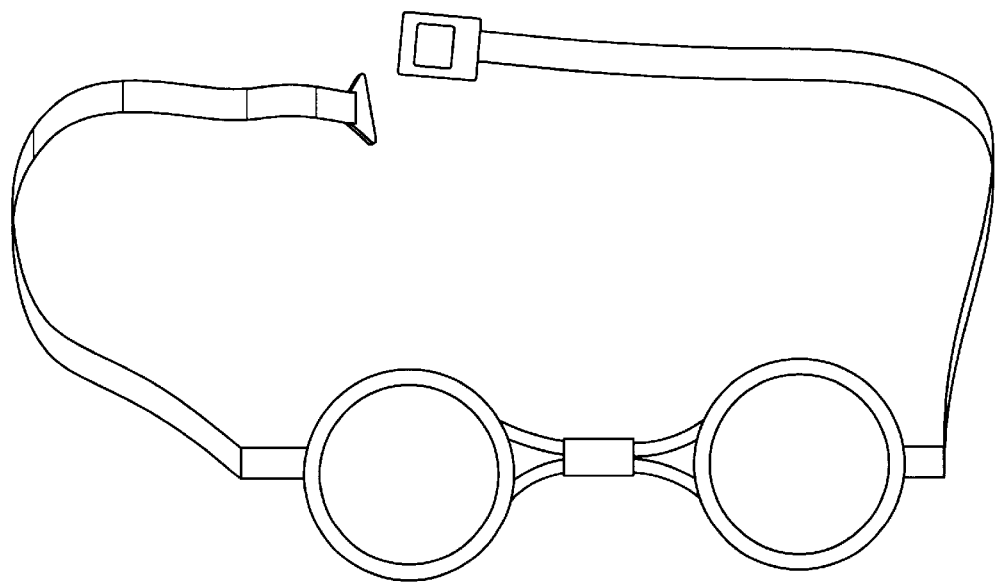
FIGS. 6A and 6B are a complete view of the two applicators assembled with the flexible eight and the straps and clutch for a back treatment.
Figure 6B:
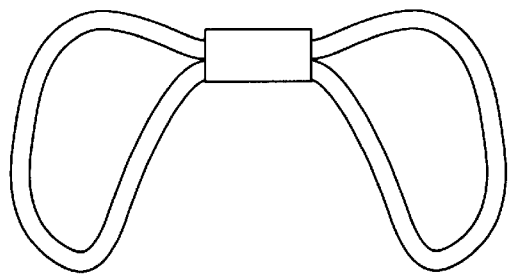
Figure 8A:
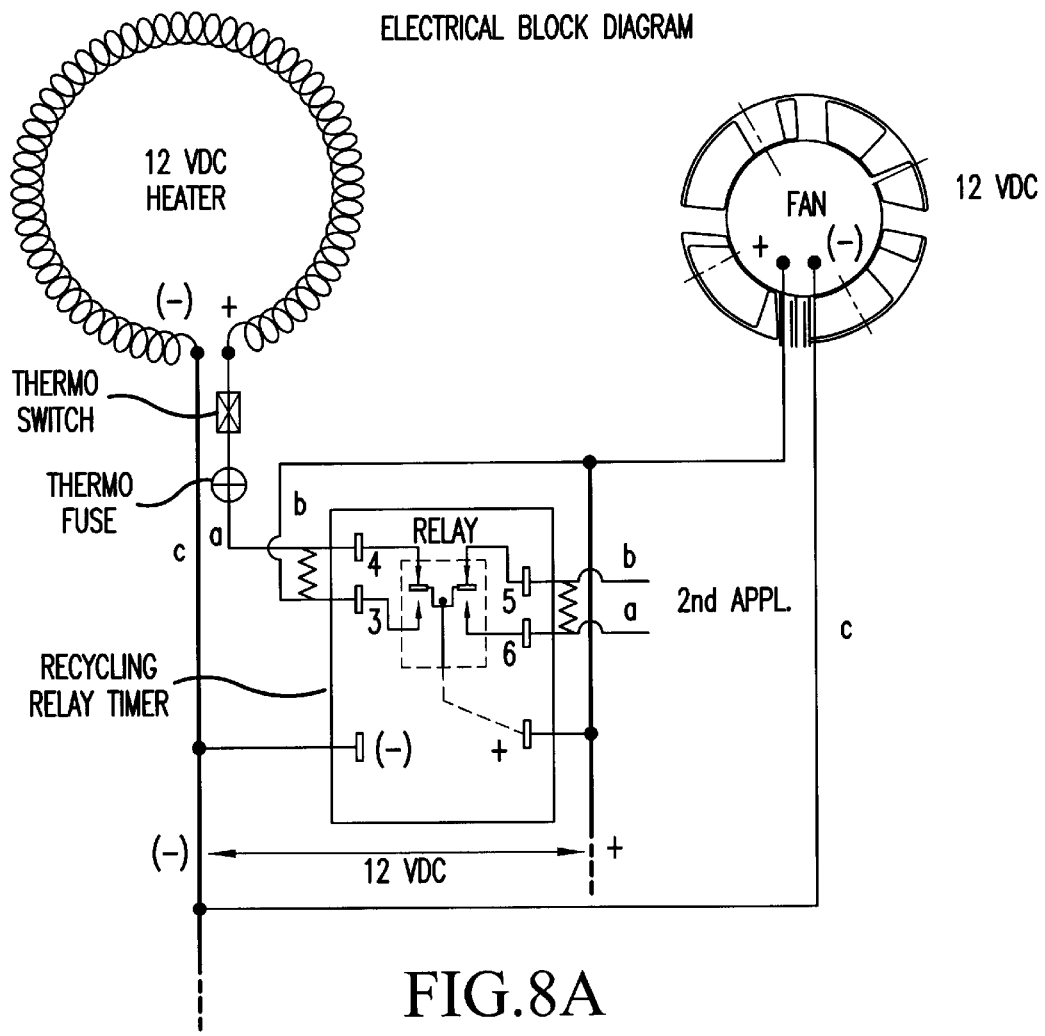
FIG. 8A is a Block Electrical Diagram.
Figure 8B:
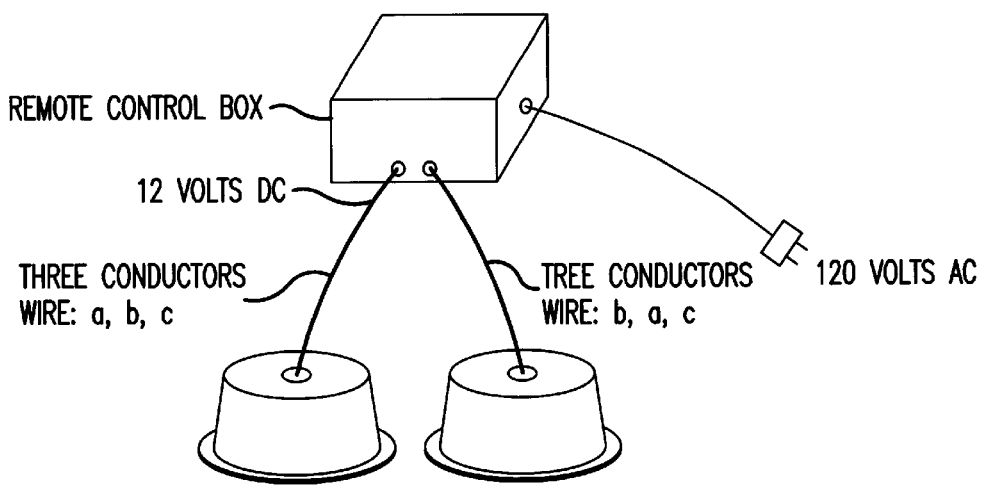
FIG. 8B shows the different components to facilitate the interpretation of functioning.

The low power required by the unit with two applicators (15 Watts±10%), the small weight and size of the unit allows the use of a flexible belt, FIG. 4. The use of the flexible belt solves a major problem of the therapy's treatment. Thus the patient will not require help from a third party to perform such treatment specially when it refers to the different parts of the body. See FIGS. 6, 7, 8. The belt makes it unnecessary to use the arms for support in order to hold the applicators and avoids the possibility of the applicator from being separated from the skin (air infiltration).

While the Flash Technique has been described in accordance with the invention, it will be appreciated that many changes may be made therein without departing from the spirit of the invention.

We claim:

1. An applicator adapted to apply a sharp peak of temperature by means of a FLASH of hot air accumulated in four to five cubic inches of air volume in a first plenum, heated by a heater located in the same plenum, the hot air is pulsed Flash peak air applied to a localized skin area of a living body which causes the heat energy to penetrate the body to a problem region underlying the skin area without unduly raising the temperature of the skin area, said applicator comprising:
   a) a casing dome having a roof and an open base and a longitudinal axis which passes through the roof and the base, said base when the applicator is in use rests on top of the skin defining an hermetic unit, conforming any uneven surface of the skin is a disposable film attached to the base of the dome, and
   b) an integrated module attached to the roof of the casing dome on the axis, said module connected to the top PCBA disc, ceramics supporting a heater coil, one metallic or plastic disc rounded in the edges, a DC tube axial fan, other discs sandwiching the fan, closing with formed guards.

2. The applicator as set forth in claim 1, wherein,
   the PBCA disc, the disc in the negative suction side of the fan separated for the ceramic and the casing walls form the negative pressure first plenum,
   the disc in the positive side of the fan, the skin and the walls form the positive pressure second plenum, and
   the inside volume of both plenums is identical ±10%.

3. The applicator as set forth in claim 2, wherein the PCBA holds a thermo-sensor and a thermo-fuse for protecting against excessive heat and temperature, and the electric circuitry facing the first plenum.

4. The applicator as set forth in claim 2, wherein the PCBA electric circuitry through a male plug attached to the dome is connected to a remote control box by means of a three fine wires cable and to the female side of the plug.

5. The applicator as set forth in claim 4, wherein the remote control box comprises a 12 volt, 15 watt rechargeable battery, a 120 AC-12 VDC charger, a on/off switch, a delay electronic timer (0 to 30 minutes) to control the treatment time, a recycling relay on/off delay delay timer to control the heater and fan sequence and duration of both cycles.

6. The applicator as set forth in claim 1, wherein the OD of the two rounded shaped discs are smaller than the ID of the casing walls, defining a ring opening for the circulation of the air.

7. The applicator as set forth in claim 1, wherein one or two applicators are supported against different parts of the body by a flexible belt and straps.

8. An applicator as set forth in claim 7, wherein a center part of the belt is a flexible plastic molded in one piece with a figure eight shape to hold two applicators inside of the circular section of a figure eight plastic piece.

9. The applicator as set forth in claim 1, wherein,
   the PBCA disc, the disc in the negative suction side of the fan separated for the four ceramic and the casing walls form the negative pressure first plenum,
   the disc in the positive side of the fan, the skin and the walls form the positive pressure second plenum, and
   the inside volume of both plenums is identical ±10%.

10. The applicator as set forth in claim 1, wherein the OD of the two rounded shaped discs are smaller than the ID of the casing walls, defining a 3/16" ring opening for the circulation of the air.

11. An applicator adapted to apply a sharp peak of temperature by means of a FLASH of hot air accumulated in four to five cubic inches of air volume in a first plenum, heated by the heater located in the same plenum, the hot air is pulsed Flash peak air applied to a localized skin area of a living body which causes the heat energy to penetrate the body to a problem region underlying the skin area without unduly raising the temperature of the skin area, said applicator comprising:
   a) a casing dome having a roof and an open base and a longitudinal axis which passes through the roof and the base, said base when the applicator is in use rests on top of the skin defining an hermetic unit, conforming any uneven surface of the skin is a disposable nitril plastic film, attached to the base of the dome, and
   b) an integrated module attached to the roof of the casing dome on the axis, said module integrated by four screws holding successively the top PCBA disc, ceramics supporting a heater coil, one metallic or plastic disc rounded in the edges, a DC tube axial fan, other disc sandwiching the fan, closing with a wire formed guards.

12. A method for heat penetration into tissues of a body without damaging skin, which comprising applying peaks of hot air to said body with the applicator of claim 1.

* * * * *